United States Patent [19]
Wadsworth, Jr. et al.

[11] Patent Number: 5,399,168
[45] Date of Patent: Mar. 21, 1995

[54] IMPLANTABLE PLURAL FLUID CAVITY PORT

[75] Inventors: Daniel C. Wadsworth, Jr., Salt Lake City; Kelly J. Christian, Sandy, both of Utah; Augustus Felix, Providence, R.I.; Patricia A. Bassett; Craig S. Nevers, both of Warwick, R.I.

[73] Assignee: C. R. Bard, Inc., Murray Hill, N.J.

[21] Appl. No.: 922,534

[22] Filed: Jul. 29, 1992

Related U.S. Application Data

[63] Continuation-in-part of Ser. No. 753,179, Aug. 29, 1991.

[51] Int. Cl.⁶ .............................................. A61M 5/32
[52] U.S. Cl. .................................. 604/175; 604/244; 604/283
[58] Field of Search .......................... 604/93, 173–175, 604/244, 283, 80; 285/242

[56] References Cited

U.S. PATENT DOCUMENTS

| | | | |
|---|---|---|---|
| 3,210,101 | 10/1965 | Bahr | 285/258 |
| 3,262,721 | 7/1966 | Knight | 285/174 |
| 3,310,051 | 3/1967 | Schulte | 128/216 |
| 3,461,869 | 8/1969 | Hargest | 128/214 |
| 3,724,882 | 4/1973 | Dehar | 285/243 |
| 3,768,102 | 10/1973 | Kwan-Gett et al. | 3/1 |
| 3,826,257 | 7/1974 | Buselmeier | 128/214 R |
| 3,958,557 | 5/1976 | Sharp et al. | 128/1 |
| 4,122,858 | 10/1978 | Schiff | 128/348 |
| 4,133,312 | 1/1979 | Burd | 128/214 R |
| 4,190,040 | 2/1980 | Schulte | 128/1 |
| 4,306,545 | 12/1981 | Ivan et al. | 128/1 R |
| 4,344,435 | 8/1982 | Aubin | 128/350 R |
| 4,405,305 | 9/1983 | Stephen et al. | 604/49 |
| 4,405,320 | 9/1983 | Cracauer et al. | 604/175 |
| 4,464,178 | 8/1984 | Dalton | 604/174 |
| 4,564,222 | 1/1986 | Loker et al. | 285/243 |
| 4,569,675 | 2/1986 | Prosl et al. | 604/175 |
| 4,632,435 | 12/1986 | Polyak | 285/243 |
| 4,635,973 | 1/1987 | Sauer | 285/242 |
| 4,673,394 | 6/1987 | Fenton, Jr. et al. | 604/175 |
| 4,675,006 | 6/1987 | Hrushesky | 604/174 |
| 4,681,560 | 7/1987 | Schulte et al. | 604/9 |
| 4,685,905 | 8/1987 | Jeanneret nee Aab | 604/247 |
| 4,692,146 | 9/1987 | Hilger | 604/93 |
| 4,693,707 | 9/1987 | Dye | 604/111 |
| 4,695,273 | 9/1987 | Brown | 604/173 |
| 4,695,276 | 9/1987 | Shinno et al. | 604/283 |
| 4,704,103 | 11/1987 | Stöber et al. | 604/175 |
| 4,710,174 | 12/1987 | Moden et al. | 604/175 |

(List continued on next page.)

FOREIGN PATENT DOCUMENTS

| | | |
|---|---|---|
| 0134745 | 3/1985 | European Pat. Off. . |
| 0157906 | 10/1985 | European Pat. Off. . |
| 343910 | 11/1989 | European Pat. Off. . |
| 366814 | 5/1990 | European Pat. Off. . |
| 2586569 | 3/1987 | France . |
| 3048892 | 7/1982 | Germany . |
| WO90/14118 | 11/1990 | WIPO . |

*Primary Examiner*—John D. Yasko
*Assistant Examiner*—Mark Bockelman
*Attorney, Agent, or Firm*—Workman, Nydegger & Seeley

[57] ABSTRACT

A subcutaneous implantable access port is formed of a housing having a pair of noncircular fluid cavities enclosed therein by a floor, walls upstanding from the floor, and a self-sealing septum positioned above each fluid cavity. The housing is constructed of a base, a septum support, and a cap. An outlet stem exits the base and communicates with the fluid cavities therein. The outlet stem has two prongs formed in a side-by-side configuration extending outwardly from the base. The prongs are formed within the stem channels in fluid communication with the fluid cavities. Protruding radially outwardly from the portion of said prong is a barb. Fluid injected into the fluid cavity through the septum flows through a smooth transition region in which the cross-sectional area is smoothly reduced from the corresponding fluid cavity. A locking sleeve provides radial inward pressure upon the catheter which is slid over the outlet stem, thereby insuring that the catheter remains mounted on the outlet stem.

39 Claims, 10 Drawing Sheets

U.S. PATENT DOCUMENTS

| | | | |
|---|---|---|---|
| 4,723,948 | 2/1988 | Clark et al. | 604/283 |
| 4,762,517 | 8/1988 | McIntyre et al. | 604/175 |
| 4,772,270 | 9/1988 | Wiita et al. | 604/283 |
| 4,772,276 | 9/1988 | Wiita et al. | 604/283 |
| 4,778,447 | 10/1988 | Velde et al. | 604/29 |
| 4,778,452 | 10/1988 | Moden et al. | 604/93 |
| 4,781,693 | 11/1988 | Martinez et al. | 604/175 |
| 4,816,020 | 3/1989 | Brownell | 604/97 |
| 4,820,288 | 4/1989 | Isono | 604/280 |
| 4,822,341 | 4/1989 | Colone | 604/175 |
| 4,826,477 | 5/1989 | Adams | 604/4 |
| 4,861,341 | 8/1989 | Woodburn | 604/175 |
| 4,880,414 | 11/1989 | Whipple | 604/283 |
| 4,892,518 | 1/1990 | Cupp et al. | 604/93 |
| 4,905,682 | 3/1990 | Khayat | 604/175 |
| 4,911,696 | 3/1990 | Miyasaka et al. | 604/244 |
| 4,915,690 | 4/1990 | Cone et al. | 604/93 |
| 4,929,236 | 5/1990 | Sampson | 604/175 |
| 4,955,861 | 9/1990 | Enegren et al. | 604/141 |
| 4,963,133 | 10/1990 | Whipple | 604/283 |
| 5,026,344 | 6/1992 | Dijkstra et al. | 604/93 |
| 5,041,098 | 8/1991 | Loiterman et al. | 604/93 |
| 5,045,060 | 9/1991 | Melsky et al. | 604/175 |
| 5,084,015 | 1/1992 | Moriuchi et al. | 604/93 |
| 5,108,377 | 4/1992 | Cone et al. | 604/175 |
| 5,167,638 | 12/1992 | Felix et al. | 604/175 |
| 5,178,612 | 1/1993 | Fenton, Jr. | 604/175 |
| 5,213,574 | 5/1994 | Tucker | 604/93 |

IMPLANTABLE PLURAL FLUID CAVITY PORT

RELATED APPLICATION

This application is a continuation-in-part application of copending U.S. patent application Ser. No. 753,179, entitled "IMPLANTABLE DUAL ACCESS PORT WITH TACTILE RIDGE FOR POSITION SENSING," which was filed on Aug. 29, 1991 still pending, and now names as inventors Arnold S. Leonard and Daniel C. Wadsworth, Jr.

BACKGROUND

1. The Field of the Invention

The present invention relates generally to a subcutaneously implantable access port. More specifically, the present invention relates to an access port having a plurality of needle-penetrable, self-sealing septums, each affording repeated access to a corresponding plurality of distinct fluid cavities each in communication with a plural lumen catheter.

2. Background Art

A variety of implantable devices, known as subcutaneous access ports, are utilized to deliver fluids to or to withdraw fluids from the bloodstream of a patient.

Such access ports typically include a needle-impenetrable housing which encloses one or more fluid cavities and defines for each such fluid cavity an access aperture communicating through the housing on the side thereof which is adjacent to the skin of the patient when the access port is implanted in the body thereof.

A needle-penetrable septum is received in and seals each access aperture. Exit passageways located in an outlet stem communicate with each of the fluid cavities for dispensing medication therefrom to a predetermined location in the body of the patient through an implanted catheter attached to the access port.

Once the access port and the catheter have been implanted beneath the skin of a patient, quantities of medication or blood may be dispensed from one such fluid cavity by means of a non-coring needle passed through the skin of the patient and penetrating the septum into one of the respective fluid cavities. This medication is directed in the distal end of the catheter to an entry point into the venous system of the body of the patient.

Blood may also be withdrawn for sampling from the body of a patient through such an access port. This is accomplished by piercing the skin of the patient and one of the respective septums with a non-coring needle and applying negative pressure thereto. This causes blood to be drawn through the catheter into the fluid cavity corresponding to the pierced septum and then out of the body of the patient through the needle.

To prevent clotting thereafter, the withdrawal route is flushed with a saline solution or heparin using again a non-coring needle piercing the skin of the patient and the septum in the same manner as if a medication were being infused.

Both intermittent and continual injections of medication may be dispensed by the access port. Continual access involves the use of a non-coring needle attached to an ambulatory-type pump or a gravity feed IV bag suspended above the patient. The ambulatory-type pump or the IV bag continually feeds the medication or fluid through the needle to the fluid cavity in the access port and from there through the catheter to the entry point into the venous system.

To facilitate locating each respective septum once the access port has been implanted, some access ports incorporate a raised circular ring located about the entire outer perimeter of the septum. This raised ring enhances the tactile sensation afforded by the subcutaneous septum to the palpating fingertip of a medical practitioner.

One problem encountered with the use of a raised ring, however, is that tissue located within the area encircled by the ring does not receive a sufficient quantity of blood. This lack of adequate blood flow may lead to necrosis of the encircled tissue. Necrosis adversely affects the localized tissues, and interferes with the passage of a needle therethrough, as well as destabilizing the pocket in which the access port is implanted.

A related problem arises as a physician attempts to access the septum during use. While a physician may tactually locate the septum through the use of such a raised ring, the natural tendency to avoid missing the septum with the needle causes most physicians to direct the needle through the septum at a point near the raised ring. While the useful life of the self-sealing septum is usually over one thousand penetrations, this assumes that the penetration will be randomly distributed over the surface of the septum. In concentrating the needle punctures near the perimeter of the septum next to the raised ring, the useful life of the septum is dramatically reduced.

Although the raised ring allows a physician to determine the location of the septum by touch, the portion of the septum that can be positively identified is usually only the perimeter of the rubberized septum, which is typically circular. As a result, the location of one septum does not in any way indicate in which direction the second septum is located.

To preclude reaction with the tissues in the body of a patient, access ports are constructed of nonreactive materials, such as titanium or stainless steel. Although these materials are nonreactive, access ports constructed utilizing titanium or stainless steel materials produce an interfering or blurred image of the body of the patient in the vicinity of the implanted access port when diagnostic imaging techniques such as magnetic resonance imaging (hereinafter "MRI"), CAT scans, or computerized tomography are used. The blurred region caused by the presence of a metallic access port in the body of a patient extends beyond the access port itself. Therefore, the use of metallic access ports limits the diagnostic imaging techniques that may be used relative to those areas of the body in which an access port is implanted. In place of metallic materials some access ports have been fabricated at least in part from biocompatible plastics.

A further problem relating to the materials for and manufacture of access ports is the deleterious impact of some manufacturing procedures on the fluids which flow through the fluid cavities and related structures located between the fluid cavities and the catheter. During the manufacture of an access port, whether the port is comprised of metallic or plastic materials, it becomes necessary to form the fluid cavities and exit passageways through which the fluid will be directed into the attached catheter.

This manufacturing process often leaves sharp edges and corners in the areas where the fluid cavity is to direct the flow of the fluid through an exit passageway. As blood or other fluids are injected through the septum into the fluid cavity, pressure developed within the fluid cavity tends to cause fluid to flow through the exit passageway. As the fluid in the fluid cavity flows past the sharp edges and corners produced in a manufacture of the access port, turbulence arises, taking the form of a vortex, adjacent to the sharp edges and corners. Some fluids, such as blood, are sensitive to this turbulence, and lysing of the red blood cell component of the injected blood can occur in these turbulent areas.

In addition, the machining of the circular fluid cavities often results in the creation of areas within the housing in which fluid flow is retarded. These areas are referred to as dead spaces and usually occur in areas of transition, such as where the bottom of the septum interfaces with the walls of the fluid cavity and where the floor of the fluid cavity meets the exit passageway through which the fluid must flow. As the flow of fluids through dead spaces is retarded, stagnation occurs, resulting in some fluid being trapped within these dead spaces. If the access port is used to transfuse blood, blood trapped in these dead spaces may form clots and block the flow of fluid through the fluid cavity.

A further problem encountered in the design and construction of access port relates to the positioning of the septums within the housing of the access port. The positioning of the septums within the housing is a compromise between two conflicting objectives. These are the need to separate the septums to such a distance so that the septums may be easily differentiated for the purpose of injection and the need to restrict the overall dimensions of the access port, which must be placed within a tissue pocket of fairly small dimensions.

The distancing of the septums to facilitate their differentiation, however, results in a corresponding distancing of the fluid cavities. This result is at odds with another structural requirement for access ports with plural cavities, namely that the exit passageways from each fluid cavity be closely spaced at the point where the implanted catheter is to be coupled to the access port.

To guide the flow of a fluid from each of the spatially separated fluid cavities into the side-by-side configuration of fluid outflow necessitated by the dimensions of a plural lumen catheter, intermediate structural members have been required. Naturally, this complicates the process of manufacture and increases its cost, as well as the chances of structural failure.

There are several examples of such intermediate members used to resolve the manufacturing constraints imposed upon the construction of a passageway flowing from spatially separate fluid cavities into a side-by-side configuration acceptable by a catheter.

One is to produce passageways in the form of bent metal tubes which are then insert molded or welded into the larger body of the access port. The use of such a metal component will interfere with the production of an access port which is free of limits as to the diagnostic imaging techniques that may be used relative to those areas of the body in which an access port is implanted.

In addition, the non-integral nature of such metal outlet passageways raises the possibility of leakage of medication through the interstices between the metal tubes and the body of the access port.

Alternatively, to produce fluid flow from spatially separated fluid cavities into the closely spaced lumens of a catheter, each fluid cavity has been designed with its own spatially separated outlet stem. These outlet stems are then coupled by a hub structure for permanent attachment to the closely spaced lumens of a catheter. This type of arrangement increases the size of the overall access port and its cost of manufacture by adding thereto the necessity of fabricating and assembling the hub element.

Port connections to catheters in this manner are permanent. Accordingly, if the catheter is to be shortened by trimming that trimming must occur at the distal end of the catheter, and this precludes the use thereat of any type of specially designed tip or valve.

One additional set of problems encountered in the use of access ports relates to the actual connection of the catheter to the access port. This is most commonly effected by securing the catheter to an outlet stem protruding from the housing of the access port. In an attempt to lock the catheter to the outlet stem of the access port, thread-type systems have been developed wherein the catheter is attached to an outlet stem, and the outlet stem is then threaded into the access port. When utilizing this system, however, it is difficult to determine the amount of engagement of the catheter onto the outlet stem. Some catheter connection systems do not allow visual verification of attachment. As a result, leakage and failure can occur.

To overcome this problem, access ports are produced in which the catheter is pre-attached at the factory. While this practice alleviates many of the problems with leakage and failure due to catheter slippage, this system severely limits the type of the catheter usable with the access port. As mentioned above, this precludes the use of catheters having specialized distal tips, as the distal end of the catheter is the only end that can then be trimmed to effect its ultimate sizing. For example, catheters utilizing a Groshong ® slit valve at their distal end may not have any of the distal tip of the catheter removed without compromising the catheter.

OBJECTS AND BRIEF SUMMARY OF THE INVENTION

Accordingly, it is an object of the present invention to provide an implantable access port having few parts, wherein all the parts are comprised of the same non-metallic material.

It is another object of the present invention to provide an access port which can be used with catheters that cannot be trimmed at the distal end thereof.

It is a further object of the present invention to provide an access port allowing direct connection of the catheter without any discrete intermediate members being required for the purpose of directing fluid flow from spatially separated fluid cavities into the closely spaced lumens of the catheter.

Another object of the present invention is to provide an access port having outlet passages which are narrowly separated.

A further object of the present invention is to provide in the access port an outlet stem which is capable of positive retention of a catheter thereupon.

It is yet another object of the present invention to provide an access port having a catheter locking system which is visually verifiable.

An additional object of the present invention is to provide an implantable access port in which the flow of fluid from the fluid cavities therein passes a minimum of sharp edges or turns.

Yet another object of the present invention is an implantable access port as described which is substantially free of areas of stagnation relative to the flow of fluid from the fluid cavity thereof within the venous system.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, an implantable dual access port is provided having a housing containing a plurality of open cavities capable of retaining medicinal or other fluids such as blood.

The housing comprises a base, a septum support, and a cap configured so as to be capable of being fixedly engaged with each other.

The base has a flat floor and walls normal and upstanding therefrom. The walls define a first fluid cavity and a second fluid cavity. The first fluid cavity at least has a cross-section that is non-circular when taken in a plane parallel to the floor of the base.

The septum support is planar and configured to mate with the ends of the walls of the base opposite from the floor of the base. The septum support has formed therethrough a first septum receiving aperture positioned above the first fluid cavity and a second septum receiving aperture positioned above the second fluid cavity. Should it be necessary to utilize an access port configured to have more than two fluid cavities, the planar septum support is be configured to have formed therethrough a corresponding number of septum receiving apertures.

The cap is configured to receive the septum support and the base, forming the exterior upper housing. The cap comprises a top wall having formed therein a first septum access aperture at a position opposite the first septum receiving aperture when the septum support and the base are received in the cap.

A second septum access aperture overlies the second septum receiving aperture when the septum support and the base are received in the cap. A skirt depends from the periphery of the top wall. The skirt encloses the septum support and the walls of the base when the septum support and the base are received in the cap.

Connected to the access port is an outlet stem in which are formed two internal stem channels. These stem channels communicate respectively through individual exit passageways with the fluid cavities. Each stem channel is longitudinally formed through a separately configured prong. The prongs are separated from each other by an elongated slot that extends from the distal tip of the prongs to a point intermediate the length of the stem.

Each prong is configured on the exterior thereof with a catheter connection means. By way of example, the catheter connection means in one embodiment is a barb located on each prong, having an approximately semicircular raised surface positioned on the outside wall of the prong near the distal end thereof. The distal face of the raised surface tapers outwardly from the wall of the prong from the distal end toward the proximal end thereof.

Both prongs are configured so as to be equal to or slightly larger than the inside diameter of the catheter to be connected thereto. When the catheter is slid over the stem, the catheter expands somewhat to snugly engage the stem. A web between the lumens of the catheter enters and engages the sides of the elongated slot between the prongs. The shape of the raised surfaces of the prongs serves to prevent the catheter from slipping off of the stem.

As a further securement means, a locking sleeve is slid over the engaged catheter and stem. The locking sleeve is sized so as to snugly grip the catheter wall and urge it against the barbs on the outside surface of the stem. This action further tends to push the prongs together, thus gripping the web of the catheter in the elongated slot therebetween.

According to one aspect of the present invention, an access port of the type described is provided with a first interface means for placing the first fluid cavity in fluid flow communication with the corresponding first exit passageway and for directing from the first fluid cavity into the first exit passageway a flow of fluid having a cross-section smoothly reduced in area from the first fluid cavity to the first exit passageway. The first interface means takes the form of a transition region formed between the first fluid cavity and the first exit passageway with walls free of sharp turns or sharp edges. The transition region thus takes on a funnel-shaped configuration in a plane taken parallel to the floor of the base of the access port. When used in combination with a fluid cavity having an otherwise circular cross section in a plane parallel to the floor of the base of the access port, such a transition region results in a fluid cavity having a droplet-shaped cross section.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings.

Understanding that these drawings depict only typical embodiments of the invention and are not therefore to be considered limiting of its scope, the invention will be described and explained with additional specificity and detail through the use of the accompanying drawings in which.

DESCRIPTION OF THE PREFERRED EMBODIMENTS

Figure 1:
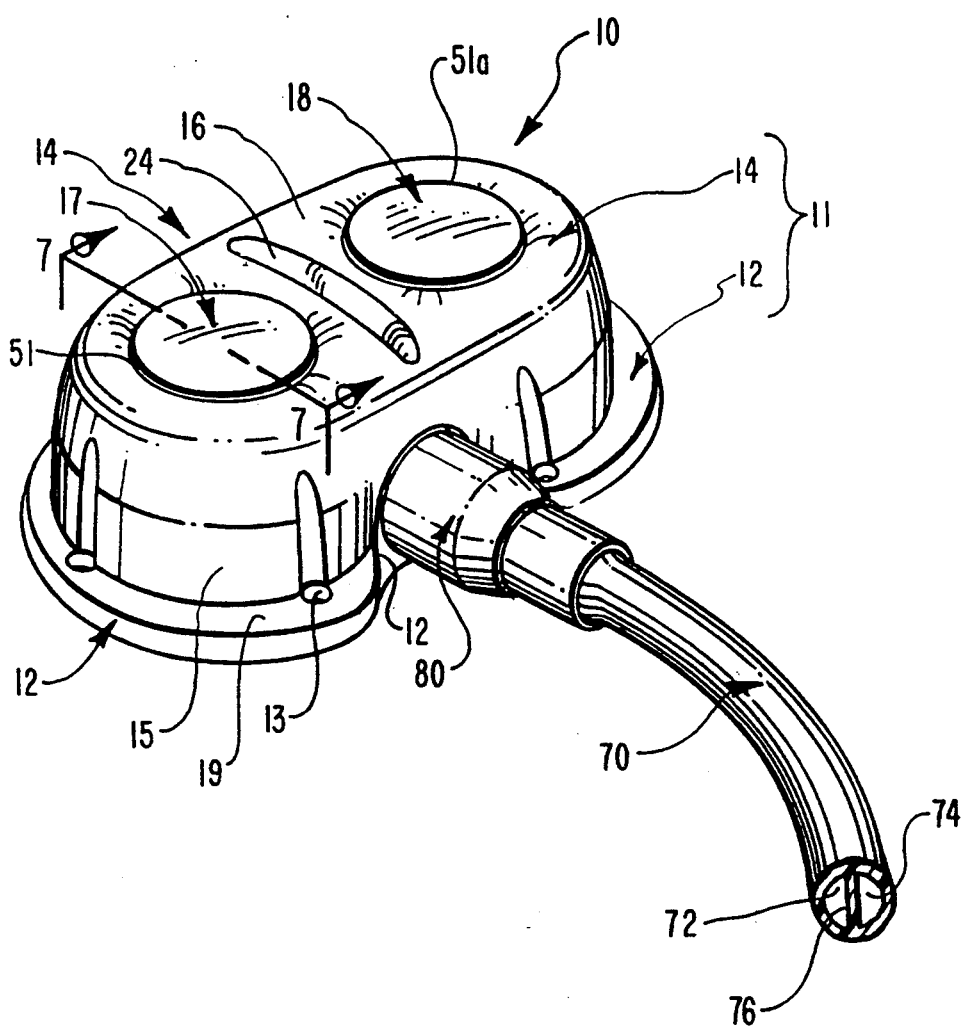
FIG. 1 is a perspective view of an implantable access port incorporating teachings of the present invention.

A perspective view of one embodiment of an implantable access port 10 incorporating teachings of the present invention is shown in FIG. 1. Access port 10 generally comprises a housing 11 which is itself comprised of three plastic components that are bonded to each other. Only two of these components, a base 12 and a cap 14, appear in FIG. 1.

During bonding, a septum support is bonded to the base after which the septums are inserted into the septum support and the cap is placed over the septum support and the walls upstanding from the base. After assembly, the bottom of the cap and the base may be bonded to form a fluid-tight joint.

An an alternate method of bonding the components of the access port involves bonding at the area surrounding the septums. After the cap has been placed over the septums, the areas near the top of the cap may be bonded to the septum support which has previously been bonded to the base.

Access port 10 also comprises a plurality of self-sealing septums, such as self-sealing septums 17 and 18, and an outlet stem not shown in FIG. 1 by which a catheter 70 is coupled to access port 10 and placed in fluid communication with fluid cavities interior thereto. Catheter 70 is a dual lumen catheter with the lumens 72 and 74 thereof, separated by a web 76.

A locking sleeve 80 enhances the lock of a catheter 70 over an outlet stem (not pictured).

In use, the distal end of catheter 70 is entered into a major vessel of the cardiovascular system of a patient and advanced therefrom, for example, into a position at the superior vena cava. After catheter 70 is thusly positioned, sufficient slack to allow for normal body movement without straining catheter 70 is left in the point of entry of catheter 70 into the vascular system. The free end of catheter 70 is then tunneled from its point of entry into the vascular system to a pocket in the tissue of a patient. The catheter is then attached to the access port, and the access port is secured into the pocket using sutures installed through suture holes 13 formed in a flange 19 about base 12. Generally, access port 10 is placed in the chest wall (infraclavicular) on either the right or the left side supported by the underlying ribs. A pocket incision is made about the length and diameter of base 12. Preferably, access port 10 is buried only about 0.50 inches below the skin, which is generally sufficient to prevent access port 10 from eroding through the skin. The pocket is then closed.

Septums 17 and 18 are configured such that they may be punctured by a non-coring needle, and re-sealed after the needle has been removed. Septums 17 and 18 are therefore constructed from a self-sealing polymer such as silicone rubber or latex.

The tactile locating of the septums 17 and 18 by a physician is facilitated in the present invention through the use of a raised ridge 24 which protrudes upwardly from cap 14. Locating ridge 24 is positioned between and closely adjacent to septums 17 and 18. In the embodiment shown in FIG. 1, raised ridge 24 is oriented so as to be orthogonal to a line joining the centers of septums 17 and 18. Such a configuration is, however, only exemplary, as various other configurations of a locating ridge are considered to fall within the scope of the present invention.

One important aspect of locating ridge 24 is that locating ridge 24 does not encircle any enclosed area of tissue. This eliminates the possibility of blood restriction and the necrosis of tissue.

Once a physician has located raised ridge 24, the physician immediately knows the location of both septums 17 and 18, namely on either side of ridge 24. It is not necessary for the physician to locate one septum, and then to have to search further for additional of the septums.

Using ridge 24 the septums can be located by tactile sensation without at the same time impeding access to the septums for the purpose of effecting an injection therethrough. This is effected by virtue of the fact that raised ridge 24 is positioned between septums 17 and 18 and does not encircle either.

Access port 10 is constructed of a plastic material which does not interfere with MRI or CAT scan diagnostic imaging. Cap 14 is comprised of a top wall 16 having formed therein a first septum access aperture 51 at a position opposite a first fluid cavity (not shown) in base 12 when base 12 is received in cap 14. A second septum access aperture 51a is also formed in top wall 16, but at a position opposite a second fluid cavity (not shown) in base 12 when base 12 is received in cap 14. A skirt 15 depends from top wall 16 of cap 14 to enclose base 12 when base 12 is received in cap 14.

Septums 17 and 18 are captured in access apertures 51, 51a sealing but affording access to the fluid cavities located thereunder. Septums 17 and 18 are needle-penetrable, while the remaining portions of access port 10 are needle-impenetrable. Cap 14 is ultrasonically welded after assembly to base 12 either at top wall 16 about septums 17 and 18 or at the bottom of skirt 15.

Figure 2:
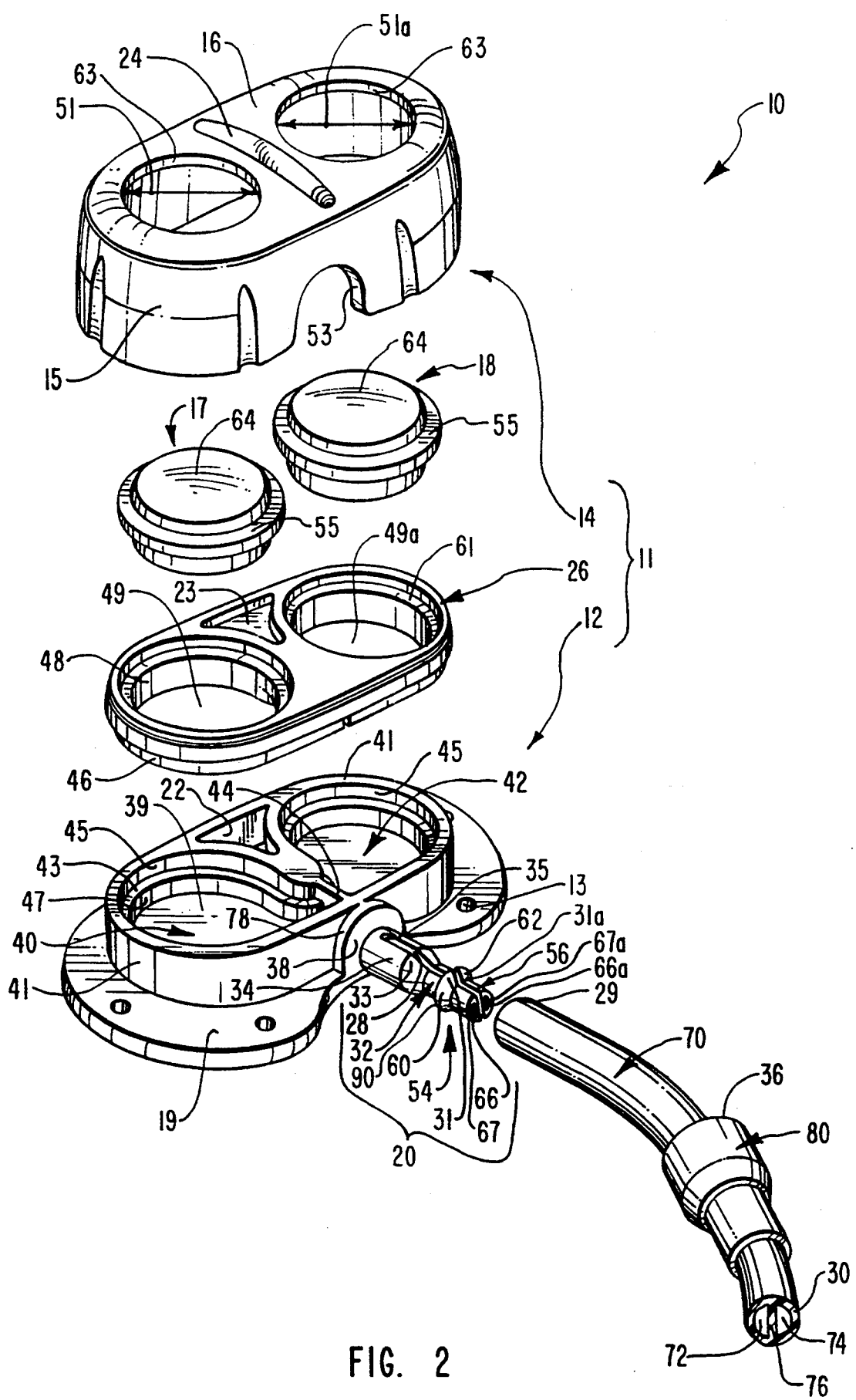
FIG. 2 is an exploded perspective view of the elements access port illustrated in FIG. 1.

A more complete depiction of the components of access port 10 is found in the exploded view thereof depicted in FIG. 2. There, access port 10 is shown to include not only base 12 and cap 14, but a septum support 26 which is disposed therebetween. Also in FIG. 2, catheter 70 is shown disconnected from an outlet stem 20 by which access port 10 and catheter 70 are connected when implanted.

Two stem channels 67 and 67a formed respectively through the lengths of prongs 54, 56, cooperate with catheter lumens 72 and 74 to couple catheter 70 to access port 10. The shape of the interior of lumens 72 and 74 corresponds to the exterior surfaces of prongs 54, 56.

Likewise, slot 28 between prongs 54, 56 corresponds in size and shape to web 76 between lumens 72, 74 of catheter 70. The entry of web 76 into slot 28 in this process results in barbs 60 and 62 being forced slightly apart, while at the same time pressure from radial exterior wall 30 of catheter 70 forces the exterior surfaces of prongs 54 and 56 inwardly onto web 76.

As proximal end 29 of catheter 70 is forced over barb ramps 31 and 31a of barbs 60 and 62, resistance increases. The outer radial edge 90 of barbs 60 and 62 has a circumference slightly larger than the inner circumference of radial exterior wall 30 of catheter 70. Pressure applied to catheter 70 in a direction toward base 12 results in the catheter sliding over barbs 60 and 62 to an area of reduced diameter 32 in which less resistance to the advancement of catheter 70 is offered.

With further force pressing catheter 70 onto outlet stem 20, proximal end 29 of catheter 70 next encounters a ramped surface 33 shown on prongs 54 and 56. As with barb ramp 31, additional force must be exerted on catheter 70 in a direction toward base 12 to urge proximal end 29 up the surface of barb ramp 31 toward a renitent surface 34. Catheter 70 is urged onto renitent surface 34 and pressed until web 76 encounters the end 35 of slot 28.

The interaction of locking sleeve 80, catheter 70, and outlet stem 20 will be discussed in more detail later in the description.

Base 12 has a flat floor 39 and generally curved walls 41 normal to and upstanding therefrom. Walls 41 define a first fluid cavity 40 and a second fluid cavity 42 having non-circular cross sections when taken at a plane parallel to floor 39. This is illustrated to better advantage and discussed at length subsequently relative to FIGS. 3 and 4.

A septum support shelf 43 serves as a stop for septum support 26 when septum support 26 is assembled on base 12. A dividing wall 44 separates fluid cavity 40 from fluid cavity 42. Dividing wall 44 shares the same longitudinal axis as slot 28 between prongs 54, 56 of outlet stem 20. Dividing wall 44 in combination with upstanding walls 41, forms a non-circular perimeter for cavities 40 and 42 in base 12 of housing 12.

Recessed walls 45 extend upward beyond septum support shelf 43 to receive the outer surface of septum support wall 46 on the side of septum support 26 that nests against base 12. Upon engagement of septum support 26 with septum support shelf 43 and recessed walls 45, the lower inner side 47 of wall 41 meets flush with the lower inner side of septum support wall 46. Thereafter, septum support 26 is bonded to base 12, preferably by ultrasonic welding. Nevertheless, in lieu thereof, alternate forms of bonding, such as adhesive bonding, may be utilized.

Septums 17 and 18 are then inserted into septum receiving apertures 49 and 49a. In so doing, fluid cavities 40 and 42 become sealed. Fluid cavities 40 and 42 are then bounded by floor 39, lower inner sidewall 47, lower inner sidewall 48, and the bottom surface of septums 17 or 18.

Figure 3:
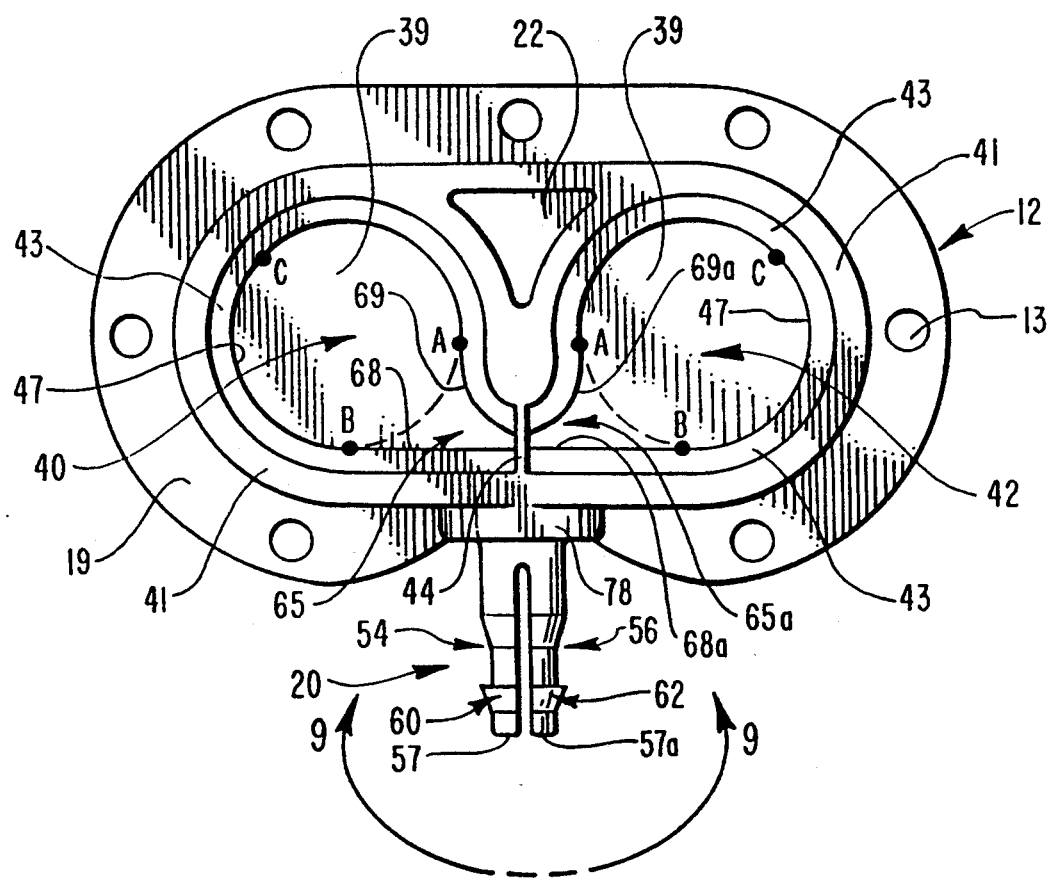
FIG. 3 is a plan view of the base of the access port illustrated in FIG. 2.

It should be noted at this point that the cross-sectional shape of fluid cavities 40 and 42 as illustrated in FIG. 3, for example, are definitively noncircular. It is one function of septum support 26 to permit the use of circular septums, such as septums 17 and 18, in conjunction with a noncircular fluid cavity, such as fluid cavities 40 and 42. Advantageously, a circular septum, such as septums 17 and 18, can be easily subjected to radially uniform support and compression, whereas a nonradially symmetric septum, such as one designed to conform to the cross-section of a noncircular fluid cavity, will be difficult to load in a radially uniform manner.

The radially uniform support and compression of a septum contributes to the equal distribution of stresses therein and to long-term, nondestructive penetration by noncoring needles.

Although much of the following discussion, for simplicity, centers around one or the other of fluid cavities 40 and 42, both cavities share the same construction. A structure in one fluid cavity is mirrored by a similar structure in the adjacent fluid cavity, as base 12 is symmetrical when viewed along a line drawn through the common longitudinal axis of dividing wall 44 and slot 28.

After septums 17 and 18 are inserted into septum receiving apertures 49, and 49a cap 14 is placed over septum support 26 and walls 41 of base 12 to enclose those structures. The bottom surface of skirt 15 of cap 14 abuts flange 19 on the exterior of walls 41. When cap 14 is bonded to base 12, the upper surfaces 64 of septums 17 and 18 protrude through access apertures 51 and 51a in top wall 16. Outlet stem 20 protrudes from a shoulder 78 on base 12 which is received in a stem arch 53 formed in skirt 15.

Septums 17 and 18 are received in septum receiving apertures 49 and 49a through the engagement of the bottom surface and sides of a septum perimeter ring 55 with the walls and top surface of a perimeter ring shelf 61 on septum support 26.

Likewise, septums 17 and 18 are retained in septum support 26 by downward pressure exerted from the engagement of the top of perimeter ring 55 by an outer perimeter 63 of access aperture 51. This allows upper surfaces 64 of septums 17 and 18 to extend beyond the top wall 16 of cap 14 and, thereby, remain accessible to a physician.

FIG. 3 is a plan view of base 12 illustrating in further detail the configuration of fluid cavities 40 and 42. Lower inner sidewall 47 comprising a circular arc ACB combines tangentially with both straight normal wall portion 68a and S-shaped convex curved wall portion 69a to form a noncircular perimeter to fluid cavity 42. Fluids injected through septum 18 enter fluid cavity 42 and travel through a transition region 65a which is bounded by minor arc AB shown in dashed lines, straight normal wall portion 68a, and S-shaped convex curved wall portion 69a.

Figure 4:
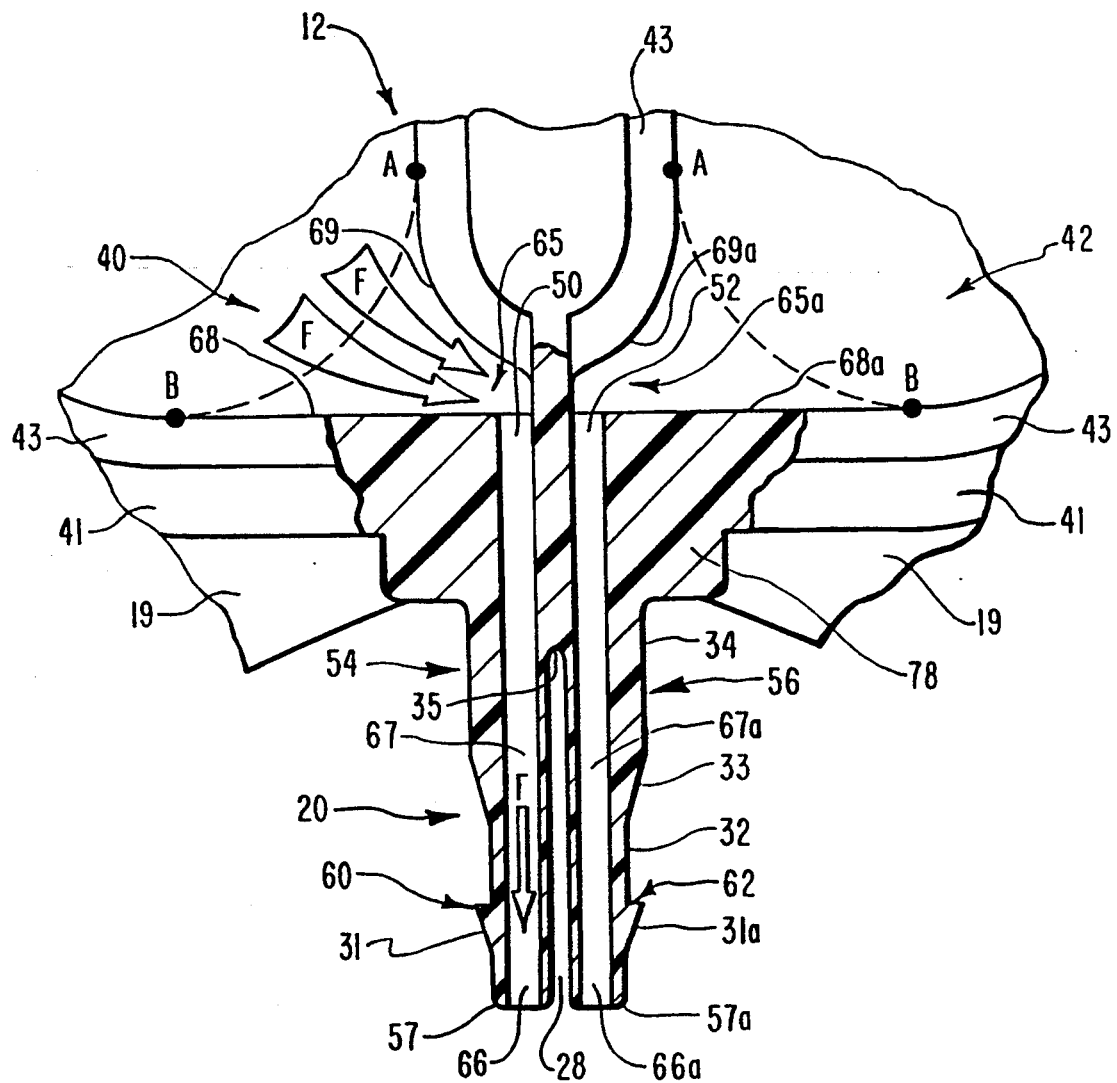
FIG. 4 is a partial breakaway plan view of the stem portion of the base illustrated in FIG. 3.

As illustrated by the arrows F in FIG. 4, the flow of the fluid out of fluid cavity 40 is directed to an exit passageway 50 located in the narrowest portion of transition region 65 and from there through the exit passageway 67 to egress point 66 at the distal tip 57 of prong 56 of outlet stem 20.

FIG. 4 illustrates a broken-away portion of outlet stem 20 showing the internal structures thereof, such as exit passageways 50 and 52, stem exit passageway 67 and 67a, and egress points 66 and 66a at distal tips 57 and 57a of each of prongs 54 and 56. Exit passageways 50 and 52 communicate respectively through stem exit passageways 67 and 67a in stem 20 with fluid cavities 40 and 42, respectively. Each stem exit passageway 67, 67a is longitudinally formed through a separately configured prong 54, 56, respectively.

Taken together, transition region 65 and 65a function as outlet means for placing fluid cavity 40 and fluid cavity 42 in fluid flow communication, respectively, with exit passageway 50 and 52 and for directing from fluid cavity 40 and fluid cavity 42, respectively, into each respective exit passageway a fluid flow having a cross-section smoothly reduced in area from each fluid cavity to the exit passageway corresponding thereto.

When a needle is inserted through either septum 17 or 18 into respective fluid cavity 40 or 42, and fluid is injected thereinto, fluid flows out of fluid cavity 40 or 42 through transition region 65 or 65a and into stem channel 67 or 67a. The velocity of flow increases in transition regions 65, 65a and is maximized at exit passageways 50 or 52. The velocity or flow rate remains constant through stem exit passageways 67 or 67a to egress points 66 or 66a at distal tips 57 and 57a of prongs 54, 56.

Transition region 65 shares floor 39 of base 12 with the fluid cavity 40. The sides of transition region 65, however, do not share the generally circular configuration of lower inner side wall 47 encircling fluid cavity 40. Instead, transition region 65 is bounded by a normal wall portion 68 disposed normal to exit passageway 50 and a convex curved wall 69 which directs the flow through fluid cavity 40 in a direction toward exit passageway 50.

Normal wall portion 68 and convex curved wall portion 69 together therefore define a transition region 65 having a cross-section that gradually reduces in area from fluid cavity 40 to exit passageway 50. It is an important aspect of the present invention that the combination of gently curved or straight walls at transition regions 65 or 65a minimizes sharp turns or edges, as well as dead spaces, in the flow of fluid out of access port 10. Once fluid has entered stem exit passageways 67 or 67a, the parallel, straight sides thereof provide a smooth passageway in which the fluid may flow.

Outlet stem 20 is formed integrally with base 12, thereby obviating any chances of leakage occurring between outlet stem 20 and base 12. No intermediate structures are required to be placed between exit passageways 50 or 52 and egress points 66 or 66a to redirect the flow of fluid from spatially separated fluid cavities 40 and 42 into the lumens of an attachable catheter. The absence of such an additional member is achieved by configuring fluid chamber 42 so that exit passageway 52 is positioned at a distance from the axis of slot 28 equal only to one-half of the thickness of web 76 of catheter 70. Correspondingly, fluid chamber 40 is configured so that exit passageway 50 is positioned at a distance from the axis of slot 28 equal only to one-half of the thickness of web 76 of catheter 70.

According to one aspect of the present invention, transition regions 65 and 65a comprise respectively first and second interface means for placing fluid cavities 40 and 42 and fluid flow communication with exit passageways 50 in 52, respectively and for directing from each respective, fluid flow cavity into the exit passageway communicating therewith a flow of fluid having a cross-section that is smoothly reduced in area from the fluid cavity to the exit passageway. Transition region 65 and 65a thus take the form generally of a funnel having a large end thereof adjacent to and communicating with fluid cavity 40 or 42 and having the small end thereof adjacent to and communicating with exit passageway 50 or 52, respectively.

As seen in overall perspective in the plan view of FIG. 3, each of fluid cavities 40 and 42 have a cross-section in a plane parallel to floor 39 of base 12 which comprises, in combination, a circle and a wedge-shaped appendage in the form of transition region 65 or 65a, having a vertex and first and second sides adjacent thereof.

In each instance, the vertex of the wedge-shaped appendage is located at exit passageway 50 or 52, respectively, away from the circular portion of the cross-section of each respective fluid cavity.

The first and second sides adjacent to the vertex join the circular portion of the cross-section at the circumference thereof. The first side of the appendage is linear, comprising normal wall portion 68, while the second side of the appendage is S-shaped, comprising convex curved wall portion 69.

Taken in another perspective, the cross-section of fluid cavity 40, 42 taken in a plane parallel to floor 39 of base 12 comprises a generally round portion substantially circled by lower inner side 47 of walls 41, a generally pointed portion remote from the round portion, and a transition region smoothly connecting the round portion to the pointed portion. In the embodiment illustrated in FIG. 3, the pointed portion of the cross-section of fluid cavities 40, 42 comprises the narrow terminus of transition regions 65, 65a at the outlet passageways. These pointed portions are disposed on the sides of fluid cavities 40 and 42 adjacent to each other, so as to terminate at a distance from each other substantially equal to the lateral separation of lumens 72, 74 of catheter 70 or egress points 66, 66a of outlet stem 20.

In other words, exit passageways 50 and 52 in the present invention are spaced apart a distance equal approximately to the width of slot 28 or web 76 between lumens 72 and 74 of catheter 70. Having exit passageways 50 and 52 so closely positioned eliminates the need for any prior art intermediary member to transition the passageways from spatially separated fluid cavities to a proximity at which a catheter may be attached directly thereto. In addition, the flow of fluid achieved out of access port 10 is free from the circuitous paths, sharp edges, or dead spaces produced by the use of such intermediary members.

Figure 5:
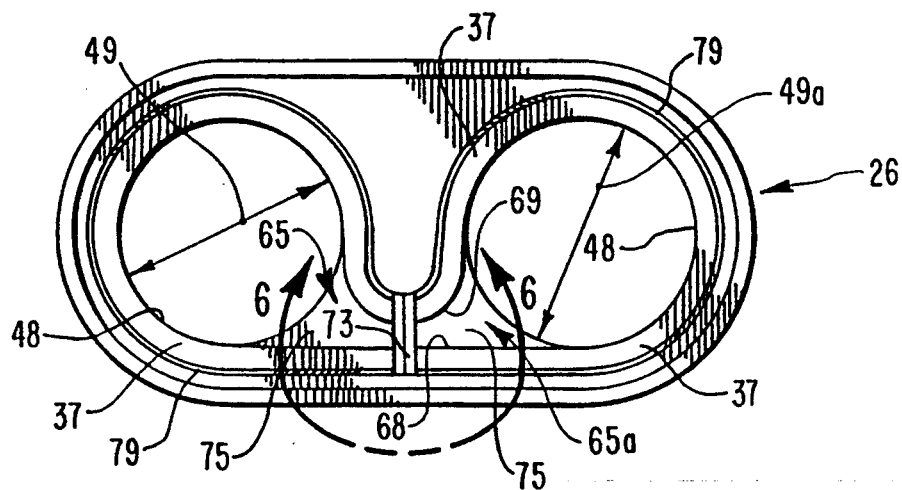
FIG. 5 is a view of the bottom surface of the septum support illustrated in FIG. 2.

FIG. 5 is a view of the bottom surface of septum support 26. It is the bottom surface of septum support 26 which nests with the tops of walls 21 of base 12 to form the fluid cavities 40 and 42. Lower inner side wall 48 of septum receiving aperture 49a forms the upper sidewall surface of fluid cavity 42. When viewed from the bottom surface as in FIG. 5, the structures forming the top of transition regions 65 and 65a may be clearly seen. Similar to the corresponding walls 41 of base 12, the normal wall portions 68 and convex curved wall portions 69 guide fluid flowing from fluid cavity 42 into exit passageway 52. As can be seen in FIG. 5, transition region 65 provides a funnel-shaped approach to exit passageway 50 which is free from sharp turns and edges. The rate of flow through transition region 65 increases as the cross-sectional area of transition region 65 is reduced. Transition region 65 is free of sharp edges and turns, which can cause turbulence and dead spaces, which can trap stagnant fluid within the fluid cavity.

Figure 6:
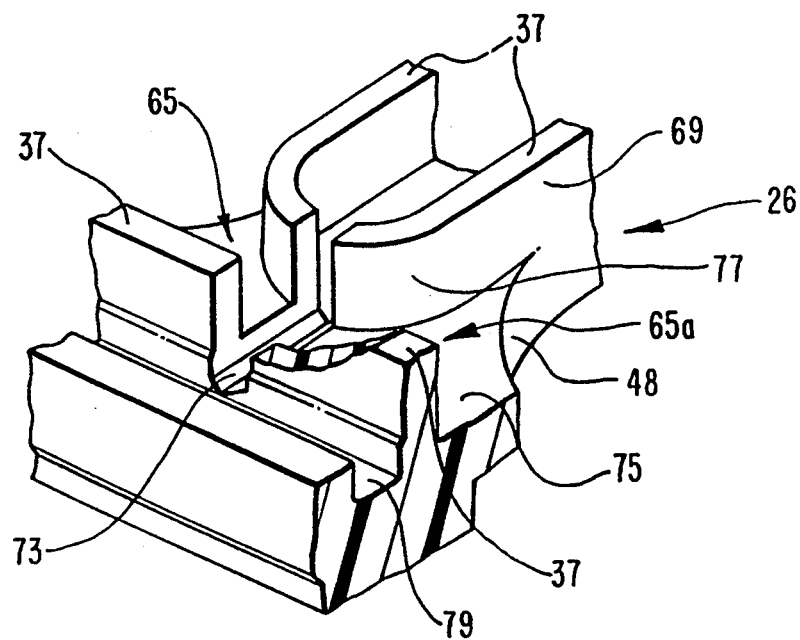
FIG. 6 is a partially broken away, cross-sectional view taken along section line 6—6 in FIG. 5.

FIG. 6 is a partially broken away enlarged view of the bottom surface of septum support 26 illustrating a receiving groove 73 shaped and sized so as to be capable of receiving dividing wall 44 of base 12. It is important to note that receiving groove 73 is very narrow, thus affording the minimum separation possible between fluid cavities 40 and 42 at the point at which transition regions 65 and 65a taper to the smallest cross-sectional area thereof at exit passageways 50 and 52, respectively. This minimal separation allows the exit passageways formed in the sides of the fluid cavities to be positioned in side-by-side configuration without the need for an intermediate structure to direct a pair of more distantly positioned exit passageways into a similar side-by-side configuration.

When assembled, receiving groove 73 on septum support 26 is filled by dividing wall 44 on base 12 and ultrasonically bonded therein.

The use of ultrasonic bonding processes to secure base 12, cap 14 and septum support 26 imposes certain structural constraints upon these components of housing 11. In a general sense, the walls of each of these three components of housing 11 must be of substantially similar thickness. In this manner, during ultrasonic bonding, all regions of the three components of housing 11 will absorb a relatively similar quantity of ultrasonic energy per volume, thereby reaching similar temperatures simultaneously.

For this reason, none of base 12, cap 14, or septum support 26 include any substantially bulky regions, and it is toward this end, for example, that base 12 is provided with a void 22 and septum support 26 is provided with a void 23 in the regions thereof intermediate fluid cavities 40 and 42 as shown in FIGS. 2 and 3.

Additionally, because ultrasonic bonding results in the generation on an almost immediate basis of molten portions of the components to be bonded, and inasmuch as those molten portions thereof tend to expand, the mating faces of base 12, cap 14 and septums 17 and 18 are provided with various voids into which such moltenized plastic can expand.

Figure 7:
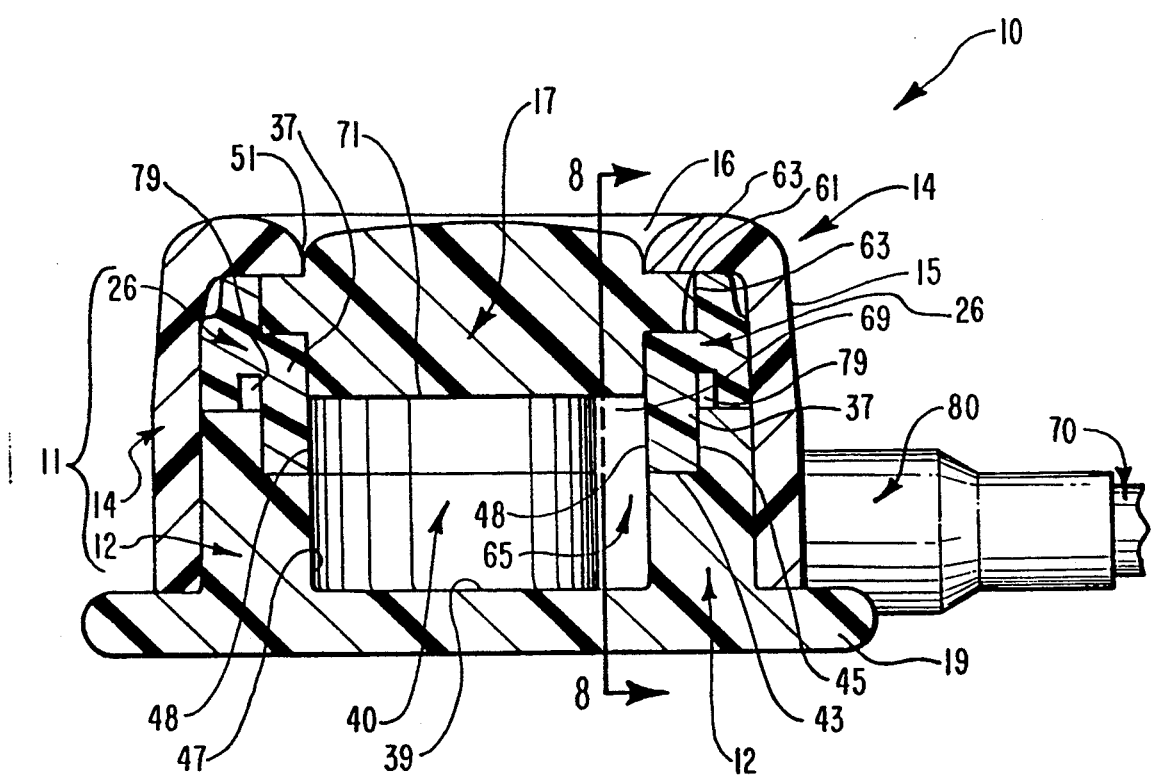
FIG. 7 is an enlarged cross-sectional elevational view of the assembled access port illustrated in FIG. 1 taken along section line 7—7 shown therein.
Figure 8:
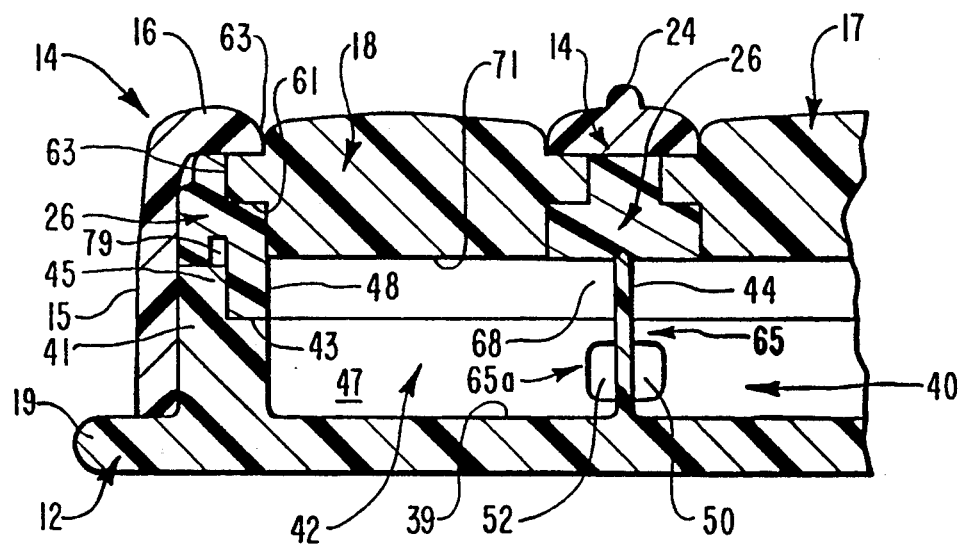
FIG. 8 is a cross-sectional, elevational view taken along section line 8—8 in FIG. 7 further illustrating the location of the septums and the geometry of the fluid cavities formed within the housing.

Thus, for example, as seen to best advantage in FIG. 5 and thereafter in FIGS. 6–8, septum support wall 37 on the lower surface of septum support 26 is encircled by a recessed flash channel 79 into which such molten plastic can expand. In this manner, molten plastic does not force apart the components being bonded together and such molten plastic flows into spaces such as flash channel 79, in preference to critical areas, such as fluid cavities 40 and 42.

Recesses 75 form the roofs of transition regions 65 and 65a when septum support 26 is affixed to base 12. Convex curved wall portion 69 has an upper portion 77 which is shaped identically to convex curved wall 69 of base 12. By joining these two walls upon assembly, transition regions 65 and 65a remain free of sharp ends and edges and directs the flow of fluid smoothly into the exit passageways.

FIG. 7 is a cross-sectional view of an assembled access port 10, such as that illustrated in FIG. 1. There, fluid cavity 40 is shown to be enclosed by floor 39 and lower inner side wall 47 of base 12, as well as lower side wall 48 of septum support 26 and a bottom surface 71 of septum 17. Transition region 65 shown in FIG. 7 to the right of the circular portion of fluid cavity 42 is shown presenting convex curved wall portion 69 to direct the flow of fluid smoothly to the right as shown in FIG. 7 into the region of reduced cross-sectional area of transition region 65 at exit passageway 52 (not shown).

Also depicted in FIG. 7 is the interaction of cap 14, septum support 26, and base 12 to form the housing 11 surrounding fluid chamber 40. When engaged, septum support 26 is in contact with septum support shelf 43. Septum 17 is supported on perimeter ring shelf 61 of septum support 26 and is permanently held down on perimeter ring shelf 61 by outer perimeter 63 of access aperture 51 in cap 14. Septum 17 is preferably held in place by the bonding of cap 14 to the top of septum support 26 or by the body of the bottom surface of skirt 15 to flange 19 of base 12.

FIG. 8 is a cross-sectional view taken along section line 8—8 in FIG. 7 to further illustrate transitional areas 65 and 65a. Septum 17 and 18 are retained between perimeter ring shelf 61 of septum support 26 and outer perimeter 63 of access aperture 51 located in cap 14. Fluid cavity 42 is shown formed between bottom surface 71 of septum 18, lower inner side wall 47 of wall 41, lower inner side wall 48 of septum support 26, and floor 39 of base 12. Normal wall portions 68 are shown adjacent each of exit passageways 50 and 52 in the transition regions 65 and 65a approaching those exit passageways. As can be seen in FIG. 8, sharp turns or edges are minimized to fluid flowing from fluid cavity 42 into exit passageway 52.

In use, a needle pierces septum 18 and fluid may then be injected into fluid cavity 42 for advancement through transition region 65a to exit passageway 52. In transition region 65, however, turbulence and vortex action is kept to a minimum and stagnation areas are avoided.

Figure 9:
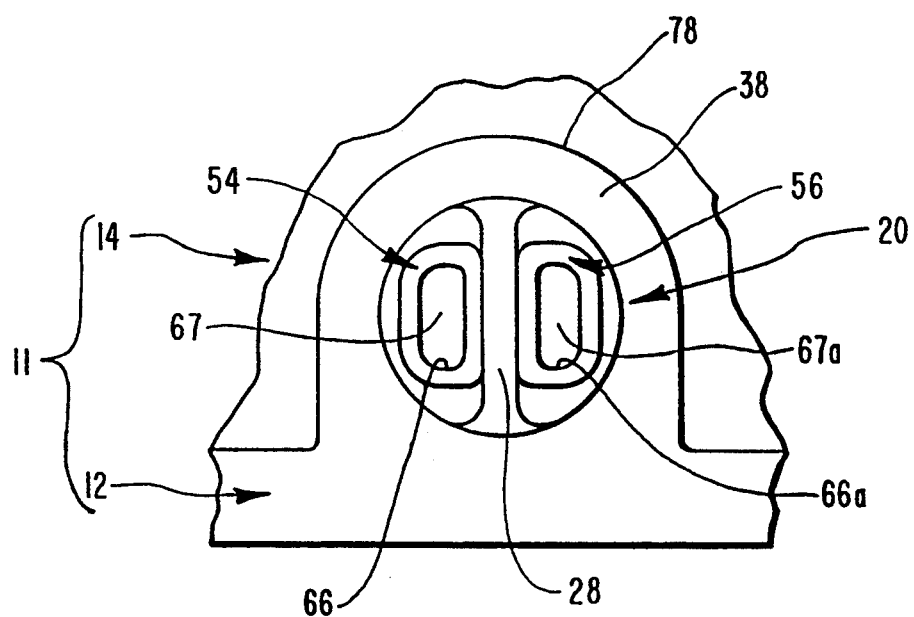
FIG. 9 is an elevational view of the outlet stem and the exit passageways formed therein when viewed along section line 9—9 in FIG. 3.

FIG. 9 illustrates an end view of outlet stem 20 having formed in each of prongs 54 and 56 thereof stem channels 67 and 67a. Slot 28 defined between prongs 54 and 56 is capable of receiving web 76 of multi-lumen catheter 70. Although the outlet stem illustrated in FIG. 9 is configured for use in a dual-lumen catheter having lumens which are generally D-shaped, catheters having a plurality of lumens having other configurations and correspondingly shaped prongs on an outlet stem also fall within the scope of the present invention. In each instance, the number and shape of stem channels 67 and 67a and the outer surfaces forming the prongs thereabout are configured so as to correspond with the number and shape of the lumens of the catheter to be slid over the prongs.

Figure 10:
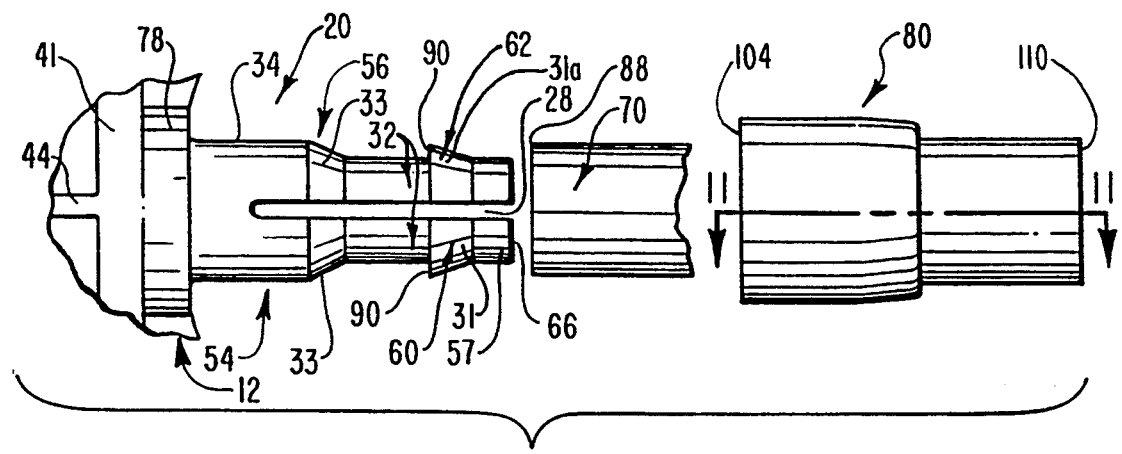
FIG. 10 illustrates the disassembled components of a system for coupling a catheter to the access port of FIG. 1.

FIG. 10 is a plan view of an outlet stem of FIG. 9 showing in disassembled state therein the catheter 70 and locking sleeve 80. To assemble these, the proximal end 88 of catheter 70 is slid over the distal tip 57 of prongs 54 and 56. As the outer diameter of prongs 54 and 56 at distal tip 57 is smaller than the internal diameter of catheter 70 at this point, a small amount of pressure is needed to engage catheter 70 over distal tip 57.

Continued pressure in the direction toward housing 11 will, however, force catheter 70 onto barb ramps 31 and 31a on barbs 60 and 62, respectively. The tip 90 of barbs 60 and 62 represents the region wherein barbs 60 and 62 have the greatest circumference. The circumference of barbs 60 and 62 at tip 90 is greater than the inside diameter of catheter 70. As a result, a great degree of resistance to the advancement of catheter 70 arises at tips 90.

Further pressure on catheter 70 in the direction of housing 11 causes proximal end 88 of catheter 70 to pass over tips 90 and onto a reduced region 32 having an outer circumference that is less than the innercircumference of catheter 70. Little resistance to the advancement of catheter 70 is encountered in this area.

As catheter 70 is advanced farther onto outlet stem 20, proximal end 88 of catheter 70 encounters a ramped surface 33, having a ramp of gradually increasing circumference terminating in a renitent surface 34. Renitent surface 34 has a circumference greater than the internal circumference of catheter 70.

Catheter 70 is inserted over outlet stem 20 to a point where the inner web 76 of the dual lumen catheter encounters the end of slot 28. Locking sleeve 80 is then slid along catheter 70 and pressed onto outlet stem 20.

Figure 11:
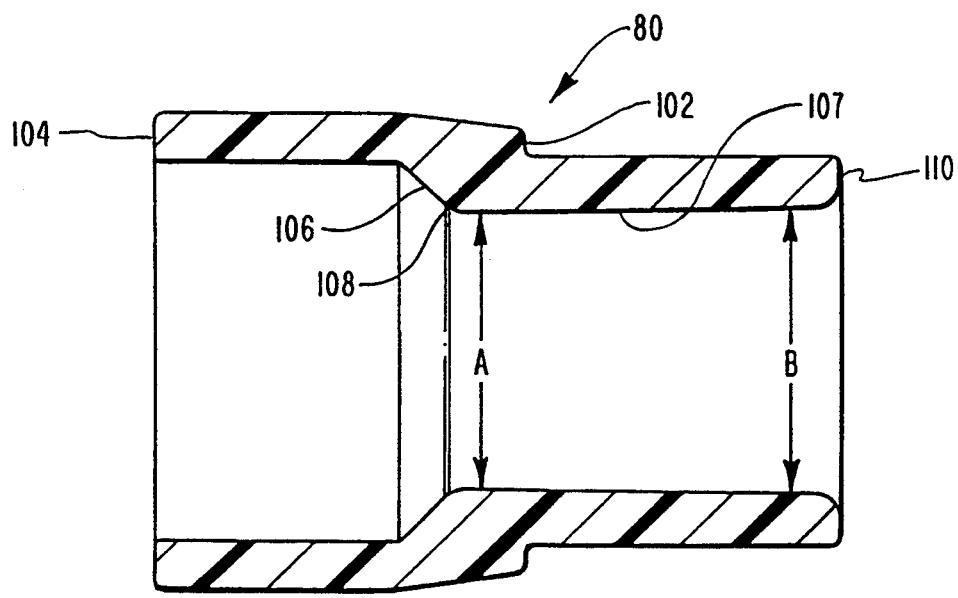
FIG. 11 is a cross-sectional view of the locking sleeve of FIG. 10 taken along section line 11—11 shown therein.

FIG. 11 is a cross-sectional view taken along section line 11—11 in FIG. 10 further depicting the inner structure of the locking sleeve 80. Although many configurations of locking sleeves fall within the scope of the present invention, a locking sleeve 80 is utilized in a presently preferred embodiment of the instant invention having on the exterior thereof a pressure application ridge 102 which provides a ridge upon which a physician may press when forcing locking sleeve 80 over catheter 70 and outlet stem 20.

To install locking sleeve 80 over catheter 70, a proximal end 104 thereof is slid over the portions of catheter 70 covering barbs 60 and 62 until proximal end 104 encounters the portion of the catheter covering ramped surface 33. As the diameter of the opening of locking sleeve 80 at proximal end 104 is greater than the diameter of tip 90 and reduced area 32, no pressure is exerted by proximal end 104 until proximal end 104 encounters the portion of the catheter covering the ramped surface 33.

Before proximal end 104 reaches ramped surface 33 and renitent surface 34, however, an internal safety ramp 106 of locking sleeve 80 begins to encounter other structures of outlet stem 20 covered by catheter 70. The diameter A of the inside of locking sleeve 80 at the narrowest point 108 of internal ramp 106 is slightly less than the diameter of tip 90 of barbs 60 and 62 when catheter 70 is slid thereover. As a result, as internal safety ramp 106 encounters the catheter covering tip 90 of barbs 60 and 62, increased resistance is encountered to the advancement of locking sleeve 80.

As internal safety ramp 106 is pressed over tips 90 of barbs 60 and 62, however, the narrowest point 108 of internal ramp 106 passes to the side of tips 90 adjacent to housing 11. From narrowest point 108 of internal safety ramp 106 to distal end 110 of locking sleeve 80 is a gradually tapering locking surface 107 along which the internal diameter B of locking sleeve 80 becomes progressively larger than diameter A. This difference between diameters A and B thus concentrates the compression of the catheter at or proximal of the barbs. As a result, energy must be introduced to remove the locking sleeve from the portion of the catheter located above the barbs. Thus, once narrowest point 108 has passed over tips 90 of barbs 60 and 62, the internal configuration of locking sleeve 80 tends to bias locking sleeve 80 to remain in position on stem 20.

The radial pressure exerted inwardly by the locking sleeve compresses barbs 54 and 56 into slot 28. This then compresses web 76 of catheter 70. The region above the barbs produces the most renitent force. This area of greatest compression also sealingly compresses the barbs against the web of the catheter.

The access port is provided with means for biasing the locking sleeve into a locking position on the outside of the catheter when the proximal end of the catheter is received on the outlet stem. By way of example and not limitation, the means for biasing provided in the embodiment illustrated in FIG. 11 comprises locking sleeve 80, internal ramp 106, and a gradually tapering surface, delineated by the surface between diameter arrow A and diameter arrow B in FIG. 11. The gradually tapering surface requires the input of energy to remove the locking sleeve from the catheter.

Figure 12:
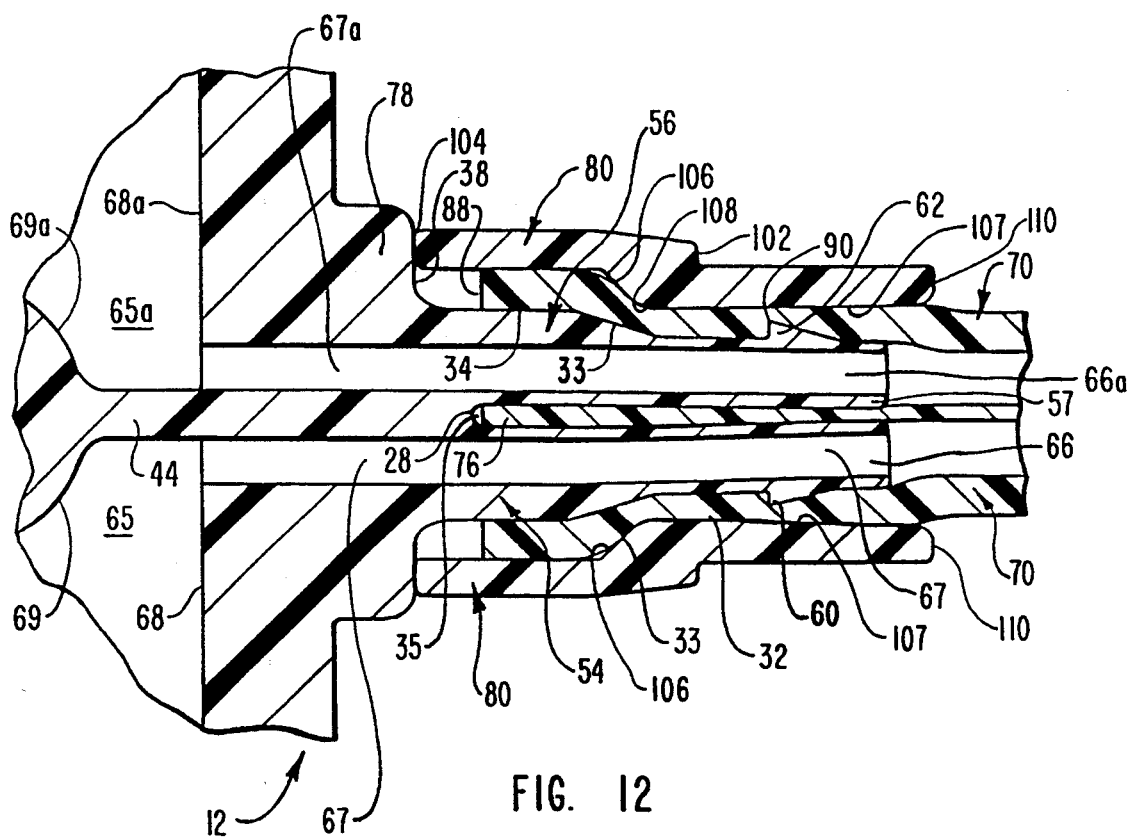
FIG. 12 is a cross-section of an assembled outlet stem, catheter, and locking sleeve like those illustrated in FIG. 10.

FIG. 12 illustrates locking sleeve 80 in its assembled position over catheter 70 on outlet stem 20. Proximal end 104 of locking sleeve 80 is shown abutted against a face 38 of shoulder 78. As the proximal end 88 of catheter 70 does not extend to this point, no pressure is exerted on outlet stem 20 there.

An area of substantially uniform pressure exists in the region where catheter 70 is in contact with renitent surface 34. Pressure exerted on prongs 54 and 56 increases in the region where internal ramp 106 is positioned in contact with ramped surface 33. As this radial pressure from the outer walls of catheter 70 forces prongs 54 and 56 together, pressure is exerted therebetween on web 76 located in slot 28 thereby sealing the interface therebetween.

The area of greatest pressure occurs in the region surrounding tip 90 of barb 60 and 62. Although the internal diameter of the locking sleeve is increasing at this point, the presence of barbs 60 and 62 greatly reduces the distance between the outer surface of prongs 54 and 56 and the inner surface of locking sleeve 80. This insures that catheter 70 and locking sleeve 80 will be retained on outlet stem 20.

Figure 13:
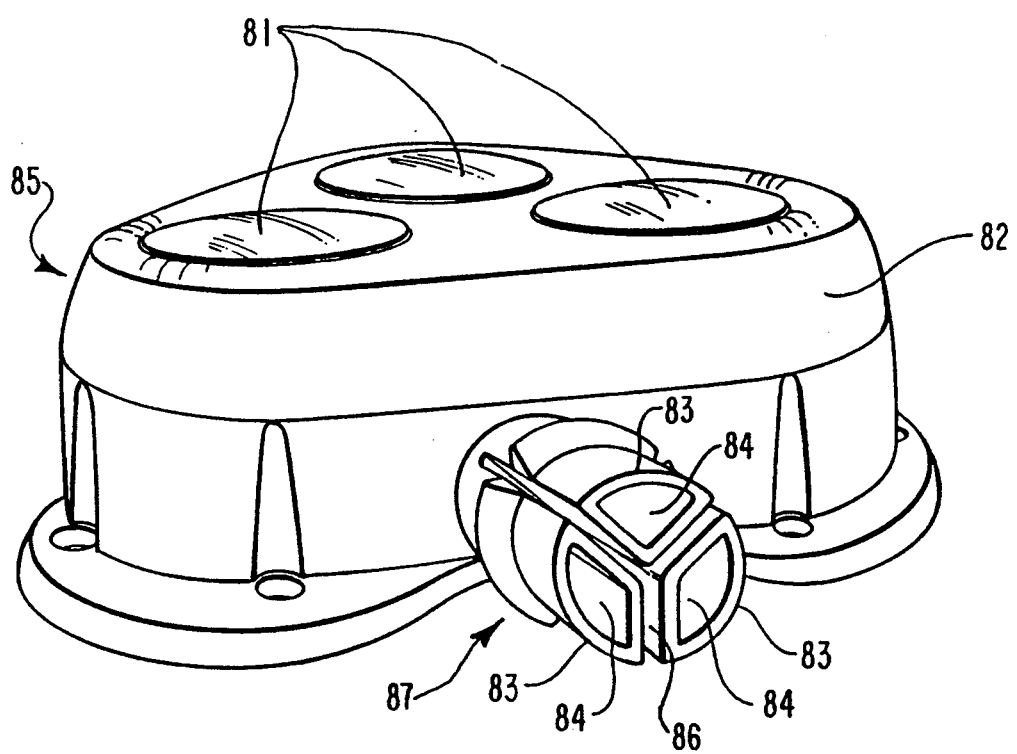
FIG. 13 illustrates an embodiment of an implantable access port capable of utilizing a triple lumen catheter.

By way of example and not limitation, a triple-cavity access port 85 capable of being utilized with a triple lumen catheter is illustrated in FIG. 13. Septums 81 are shown captured within the housing 82 thereof enclosing three fluid cavities (not pictured). An outlet stem 87 comprised of three prongs 83 provides support for a triple lumen catheter (not shown) having generally wedge or triangular shaped lumens. These communicate through egress points 84 of an exit passageway in each of outlet stems 83. Pressure exerted by the exterior wall of the catheter against the sides of prongs 83 urges these into a Y-shaped slot 86 which is filled with a Y-shaped web when a catheter is slid over this outlet stem.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An implantable access port capable of being implanted beneath the skin of a patient, the access port enabling repeated, non-destructive fluid communication between the tip of a hypodermic needle piercing the skin of the patient and the proximal end of a selected one of the lumens of a dual lumen catheter implanted in the body of the patient coupled to the access port, thereby to selectively inject a fluid from the needle into the body of the patient by producing a flow of the fluid from the tip of the needle, through the access port, and along the selected one of the lumens to the distal end of the catheter, said access port comprising:
  (a) a needle-impenetrable housing enclosing a first fluid cavity and a second fluid cavity, said housing defining a first access aperture communicating through said housing with said first fluid cavity and a second access aperture communicating through said housing with said second fluid cavity, said housing comprising:
   (i) a needle-impenetrable base having a flat interior floor and walls normal to and upstanding therefrom, said walls defining said first fluid cavity and said second fluid cavity, said first fluid cavity having a cross-section in a plane parallel to said floor of said base that is noncircular;
   (ii) a septum support configured to mate with the ends of said walls of said base opposite from said floor of said base, said septum support having formed therethrough a first septum receiving aperture positioned above said first fluid cavity and a second septum receiving aperture positioned above said second fluid cavity;
   (iii) a needle-impenetrable cap configured to receive said septum support and said base, said cap comprising a top wall having formed therein:

(A) a first septum access aperture communicating through said top wall of said cap at a position opposite said first septum receiving aperture when said septum support and said base are received in said cap, said first septum access aperture and said first septum receiving aperture together defining said first access aperture; and (B) a second septum access aperture communicating through said top wall at a position opposite said second septum receiving aperture when said septum support and said base are received in said cap, said second septum access aperture and said second septum receiving aperture together defining said second access aperture;

(b) a first needle-penetrable septum captured by said housing and sealing said first access aperture;

(c) a second needle-penetrable septum captured by said housing and sealing said second access aperture;

(d) an outlet stem connected at a proximal end thereof with said housing and configured at a distal end thereof to receive the proximal end of the catheter, said stem enclosing a first stem channel and a second stem channel, said first and second stem channels extending in side-by-side relationship between said distal and said proximal ends of said stem, the proximal ends of said first and Second stem channels being separated laterally a distance substantially equal to the lateral separation of the lumens in the catheter;

(e) a first exit passageway formed in said housing communicating with said proximal end of said first stem channel; and (f) first interface means for placing said first fluid cavity in fluid flow communication with said first exit passageway and for causing the flow of the fluid through said access port from said first fluid cavity into said first exit passageway to be substantially free of turbulence, said first interface means comprising a first transition region formed between said first fluid cavity and said first exit passageway having a lateral cross-section smoothly reducing in area along said first transition region from said first fluid cavity to said first exit passageway.

2. An access port as recited in claim 1, further comprising:

(a) a second exit passageway formed in said housing communicating with said proximal end of said second stem channel; and (b) second interface means for placing said second fluid cavity in fluid flow communication with said second exit passageway and for causing the flow of the fluid through said access port from said second fluid cavity into said second exit passageway to be substantially free of turbulence, said second interface means comprising a second transition region formed between said second fluid cavity and said second exit passageway having a lateral cross-section smoothly reducing in area along said second transition region from said second fluid cavity to said second exit passageway.

3. An access port as recited in claim 2, wherein said transition region has walls free of sharp turns.

4. An access port as recited in claim 2, wherein said transition region has walls free of sharp edges.

5. An access port as recited in claim 2, wherein said first interface means and said second interface means are located within said housing on adjacent sides of said first fluid cavity and said second fluid cavity, respectively.

6. An access port as recited in claim 1, wherein the longitudinal axis of said outlet stem is disposed in a plane normal to and bisecting of a line connecting the center of said first fluid cavity with the center of said second fluid cavity.

7. An access port as recited in claim 1, wherein said first and said second stem channels are linear.

8. An access port as recited in claim 1, wherein said first and said second stem channels are disposed in parallel relationship to each other.

9. An access port as recited in claim 1, wherein said first and said second stem channels are elliptical in cross-section.

10. An access port as recited in claim 1, wherein said housing further comprises:

(a) an interior top wall disposed opposite said interior floor of said housing and being generally parallel thereto;

(b) side walls extending from the periphery of said floor to said top wall; and (c) a dividing wall extending between said floor, said top wall, and opposed portions of said side walls, thereby to define on opposite sides of said dividing wall said first fluid cavity and said second fluid cavity, respectively.

11. An access port as recited in claim 10, wherein said first access aperture and said second access aperture are formed through said top wall of said housing, and wherein the cross-section of said first and second access apertures are circular.

12. An access port as recited in claim 10, wherein the cross-section of the Combination of said first fluid cavity said first transition region taken in a plane parallel to said floor of said housing is noncircular.

13. An access port as recited in claim 12, wherein said cross-section of said combination of said first fluid cavity and said first transition region taken in a plan parallel to said floor of said housing comprises in combination:

(a) a circle; and (b) an appendage having a vertex and first and second sides adjacent thereto, said vertex of said appendage being directed away from said circle with said first and second sides of said appendage joining said circle at the circumference thereof.

14. An access port as recited in claim 1, wherein said outlet stem comprises a proximal end and a distal end, the proximal end of said outlet stem being attached to said housing and enclosing two separate enclosed stem channels, each of said stem channels communicating with a respective one of said fluid cavities and being longitudinally formed through a separately configured prong, said prongs being spaced apart from each other by an elongate slot extending from the distal end of said outlet stem to a point intermediate the length of said outlet stem, the proximal end of said outlet stem being configured so as to snugly accept the catheter, with each lumen of the catheter communicating with a respective stem channel, and with the web of the catheter that separates the lumens thereof being received into the elongate slot between said prongs of said stem.

15. An access port as recited in claim 14, wherein said walls upstanding from said interior floor of said base further comprise a dividing wall separating said first fluid cavity from said second fluid cavity, said dividing wall having a thickness substantially equal to the lateral separation of the lumens of the catheter.

16. An access port as recited in claim 14, wherein each of said first and said second prongs comprise a barb protruding radially outwardly from an outer surface thereof.

17. An access port as recited in claim 1, wherein said base, said septum support, and said cap are provided with suitable voids and flash channels so as to enable ultrasonic bonding of said septum support to said base and of said septum support and said base inside said cap.

18. An access port as recited in claim 1, wherein said outlet stem is secured to said base.

19. An access port as recited in claim 14, wherein the cross-section of each prong corresponds to the internal cross-section of a corresponding lumen of the catheter.

20. An access port as recited in claim 1, wherein said outlet stem is formed integrally with said base.

21. An access port as recited in claim 1, wherein said base further comprises an attachment flange formed at the periphery thereof and disposed in a substantially co-planar relationship with said floor thereof.

22. An access port as recited in claim 21, wherein suture apertures are formed through said attachment flange.

23. An access port as recited in claim 1, further comprising:
(a) a first needle-penetrable septum captured between said septum support and said cap sealing said first access aperture; and
(b) a second needle-penetrable septum captured between said septum support and said cap sealing said second access aperture.

24. An access port as recited in claim 23, wherein said base, said septum support, and said cap are ultrasonically bonded to form a needle-impenetrable housing.

25. An access port as recited in claim 23, wherein said cap further comprises a skirt depending from the periphery of said top wall of said cap, said skirt enclosing said septum support and said walls of said base when said septum support and said base are received in said cap.

26. An access port as recited in claim 25, further comprising an outlet stem connected at a proximal end thereof with said housing and configured at a distal end thereof to receive the proximal end of the catheter.

27. An access port as recited in claim 26, wherein said outlet stem is integrally formed with said base.

28. An access port as recited in claim 26, wherein said outlet stem projects through said skirt of said cap generally parallel to said floor of said base when said base is received in said cap.

29. An access port as recited in claim 1, wherein the cross-section of said first fluid cavity and the cross-section of said second fluid cavity taken in a plane parallel to said floor of said base differ in shape from the cross-section of said first septum receiving aperture and the cross-section of said second septum receiving aperture, respectively.

30. An access port as recited in claim 29, wherein said cross-section of said first septum receiving aperture and said cross-section of said second septum receiving aperture are circular.

31. An access port as recited in claim 29, wherein cross-section of said first fluid cavity and said cross-section of said second fluid cavity are noncircular.

32. An implantable access port capable of being implanted beneath the skin of a patient, the access port enabling repeated, non-destructive fluid communication between the tip of a hypodermic needle piercing the skin of the patient and the proximal end of a selected one of the lumens of a dual lumen catheter, implanted in the body of the patient coupled to the access port, thereby to selectively inject a fluid from the needle into the body of the patient by producing a flow of the fluid from the tip of the needle, through the access port, and along the selected one of the lumens to the distal end of the catheter, said access port comprising:

(a) a needle impenetrable housing enclosing a first fluid cavity and a second fluid cavity, said housing having a generally planar interior floor and defining a first access aperture communicating through said housing with said first fluid cavity and a second access aperture communicating through said housing with said second fluid cavity;
(b) a first needle-penetrable septum captured by said housing and sealing said first access aperture;
(c) a second needle-penetrable septum captured by said housing and sealing said second access aperture;
(d) first and second exit passageways formed through said housing in side-by-side relationship separated laterally a distance substantially equal to the lateral separation of the lumens in the catheter; and
(e) outlet means for placing said first fluid cavity and said second fluid cavity in fluid flow communication, respectively, with said first exit passageway and said second exit passageway and for causing the flow of fluid through said access port from said first fluid cavity and said second fluid cavity, respectively into said first exit passageway and said second exit passageway to be substantially free of turbulence, said outlet means comprising:
(i) a first transition region formed interior of said housing between said first fluid cavity and said first exit passageway, said first transition region having a top surface disposed parallel to said interior floor of said housing and therebetween side surfaces tapering smoothly from said first fluid cavity to said first exit passageway, in a lateral cross-section taken parallel to said interior floor of said housing a first of said side surfaces appearing linear and a second of said side surfaces appearing S-shaped; and
(ii) a second transition region formed interior of said housing between said second fluid cavity and said second exit passageway, said second transition region having a top surface disposed parallel to said interior floor of said housing and therebetween side surfaces tapering smoothly from said second fluid cavity to said second exit passageway, in a lateral cross-section taken parallel to said interior floor of said housing a first of said side surfaces appearing linear and a second of said side surfaces appearing S-shaped.

33. An access port as recited in claim 32, wherein said side surfaces of said first and second transition regions are free of sharp turns.

34. An access port as recited in claim 32, wherein said side surfaces of said first and second transition regions are free of sharp edges.

35. An implantable access port system capable of being implanted beneath the skin of a patient, said system comprising:

(a) an access port having a housing with two fluid cavities formed therein;

(b) an outlet stem protruding from said housing and having barbs protruding radially outwardly from an outer surface thereof;

(c) a dual-lumen catheter capable of being attached at the proximal end thereof to said outlet stem by the advancement of said catheter over said barbs of said outlet stem; and (d) a locking sleeve capable of being slid over said proximal end of said catheter into a locking position of said locking sleeve, when said proximal end of said catheter has been advanced over said outer surface of said outlet stem, said locking sleeve in said locking position thereof exerting radial compression on said proximal end of said catheter and on said outlet stem, thereby to resist the removal of said catheter from said outlet stem, said locking sleeve comprising a locking surface protruding inwardly from an inner surface of said locking sleeve, said locking surface tapering gradually inwardly from the distal end of said locking sleeve to a narrowest point of said inner surface of said locking sleeve located intermediate said distal end and the proximal end thereof, said narrowest point being disposed between said housing and said barb on said outlet stem when said locking sleeve is in said locking position thereof.

36. An implantable access port system as recited in claim 35, wherein said outlet stem is connected at a proximal end thereof with said housing and is configured at the distal end thereof to receive the proximal end of said catheter, said outlet stem comprising:

(a) a plurality of prongs connected at a proximal end of each thereof to said housing, one of said prongs corresponding to each of said fluid cavities, said prongs projecting in a spaced-apart substantially parallel array from said housing with the distal ends of said prongs positioned to be receivable individually in a corresponding one of each of the lumens of said catheter, each of said prongs having a ramped surface on the exterior thereof intermediate said proximal and said distal ends of each of said prongs; and (b) a plurality of exit passageways, one of said exit passageways corresponding to and communicating with an individual one of each of said fluid cavities, each of said exit passageways communicating with a stem channel extending within an individual one of said prongs from said distal to said proximal ends thereof.

37. An implantable access system as recited in claim 36, wherein said locking surface and said narrowest point of said inner surface of said locking sleeve comprise safety means for biasing said locking sleeve into said. locking position thereof.

38. An implantable access port system as recited in claim 37, wherein said safety means further comprises a safety ramp protruding inwardly from an inner surface of said locking sleeve at a point corresponding to said ramped surface on said exterior of said prongs of said outlet stem in said locking position of said locking sleeve, thereby to tightly engage said catheter between said safety ramp of said locking sleeve and said ramped surface of each of said prongs, when said locking sleeve is in said locking position thereof.

39. An access port system as recited in claim 36, wherein a web separates the lumens of the catheter, and said locking sleeve is so configured as to compress the wall of the catheter against the outer surface of said outlet stem at a position intermediate said distal and proximal ends of said prongs, thereby to urge said prongs of said outlet stem toward each other and into engagement with the web of the catheter.

* * * * *

UNITED STATES PATENT AND TRADEMARK OFFICE
CERTIFICATE OF CORRECTION

PATENT NO. : 5,399,168

DATED : March 21, 1995

INVENTOR(S) : Daniel C. Wadsworth et al

Page 1 of 2

It is certified that error appears in the above-indentified patent and that said Letters Patent is hereby corrected as shown below:

Column 3, line 24, "access port" should be --access ports--

Column 3, line 28, delete "sc

Column 7, line 25, "An an" should be --An--

Column 10, line 4, "apertures 49, and 49a" should read --apertures 49 and 49a--.

Column 11, line 42, after "respectively" insert --,--

Column 11, line 43, after "respective" delete ","

Column 17, line 29, "Second" should be --second--

Column 17, line 61, before "smoothly" insert --taken parallel to said floor of said housing, that is asymmetrical and--

Column 18, lines 7-8, delete "disposed in a plane"

Column 18, line 34, "cross-section" should be --cross-sections--

UNITED STATES PATENT AND TRADEMARK OFFICE
CERTIFICATE OF CORRECTION

PATENT NO. : 5,399,168

DATED : March 21, 1995

INVENTOR(S) : Daniel C. Wadsworth et al

It is certified that error appears in the above-indentified patent and that said Letters Patent is hereby corrected as shown below:

Column 18, line 37, "Combination" should be --combination--

Signed and Sealed this

Seventeenth Day of October, 1995

Attest:

BRUCE LEHMAN

Attesting Officer     Commissioner of Patents and Trademarks